United States Patent [19]

Errede et al.

[11] Patent Number: 4,565,663
[45] Date of Patent: Jan. 21, 1986

[54] METHOD FOR MAKING WATER-SWELLABLE COMPOSITE SHEET

[75] Inventors: Louis A. Errede, North Oaks; James D. Stoesz, St. Paul, both of Minn.; George D. Winter, deceased, Bridgend, Wales, by Jenny Upton, legal representative

[73] Assignee: Minnesota Mining and Manufacturing Company, St. Paul, Minn.

[21] Appl. No.: 603,607

[22] Filed: Apr. 25, 1984

Related U.S. Application Data

[60] Division of Ser. No. 444,199, Nov. 23, 1982, Pat. No. 4,460,642, which is a continuation-in-part of Ser. No. 277,990, Jun. 26, 1981, Pat. No. 4,373,519.

[51] Int. Cl.$^4$ .............. B29D 27/00; B29D 7/14; B29B 1/04
[52] U.S. Cl. .............. 264/120; 264/122; 264/127; 264/175
[58] Field of Search .............. 264/127, 108, 120, 122, 264/175

[56] References Cited

U.S. PATENT DOCUMENTS

| | | | |
|---|---|---|---|
| 3,105,491 | 10/1963 | Harwood | 604/372 |
| 3,281,511 | 10/1966 | Goldsmith | 264/127 |
| 3,416,993 | 12/1968 | Heusser et al. | 428/323 |
| 3,655,853 | 4/1972 | Gallup | 264/127 |
| 3,699,103 | 6/1972 | Harper et al. | 128/156 |
| 3,888,257 | 6/1975 | Cook et al. | 128/296 |
| 3,901,236 | 8/1975 | Assarsson et al. | 128/156 |
| 4,025,679 | 5/1977 | Denny | 428/422 |
| 4,153,661 | 5/1979 | Ree et al. | 264/120 |
| 4,187,342 | 2/1980 | Holst et al. | 428/283 |
| 4,194,040 | 3/1980 | Breton et al. | 264/127 |
| 4,203,435 | 5/1980 | Krull et al. | 128/156 |
| 4,235,237 | 11/1980 | Mesek et al. | 128/284 |
| 4,385,093 | 5/1983 | Hubis | 428/323 |

FOREIGN PATENT DOCUMENTS 1454055  10/1976  United Kingdom.

Primary Examiner—James Lowe
Attorney, Agent, or Firm—Donald M. Sell; James A. Smith; Lorraine R. Sherman

[57] ABSTRACT

A method of preparing a tear-resistant composite sheet material having hydrophilic, absorptive particles enmeshed in a network of interlaced microfibrous polytetrafluoroethylene forming a fibril matrix, the hydrophilic absorptive particles having absorptive particles with absorptive capacity greater than 1.0 gram of water per gram of dry particle, wherein the method comprises:

(1) dry blending one or more hydrophilic, absorptive particulate materials;
(2) admixing water to particulate to form a damp mixture;
(3) adding gradually, with stirring, to the mixture an equal weight of an aqueous emulsion of polytetrafluoroethylene;
(4) mixing the mass to cause initial fibrillation of the polytetrafluoroethylene particles;
(5) biaxially calendering the mass to produce a tear-resistant sheet having a tensile strength of at least 0.5 megapascal; and
(6) drying the resultant sheet to remove water.

17 Claims, 1 Drawing Figure

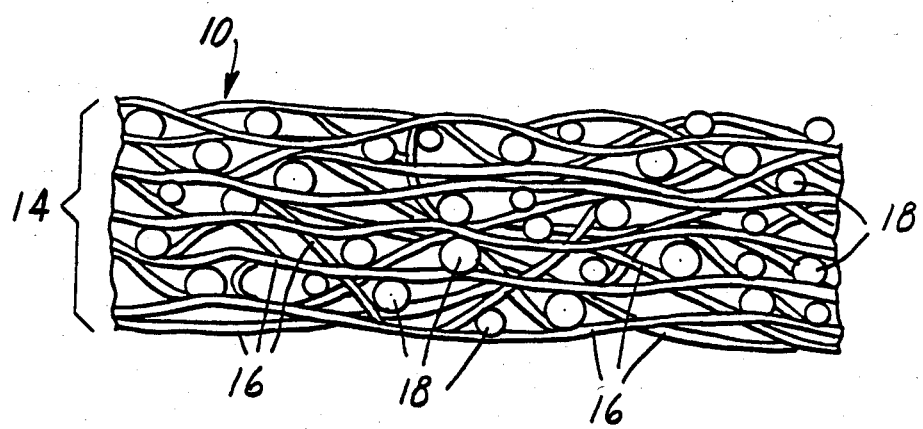

METHOD FOR MAKING WATER-SWELLABLE COMPOSITE SHEET

This application is a division of copending application U.S. Ser. No. 444,199, filed Nov. 23, 1982, now U.S. Pat. No. 4,460,642, which is a continuation-in-part of copending application U.S. Ser. No. 277,990, filed June 26, 1981, now U.S. Pat. No. 4,373,519.

TECHNICAL FIELD

The present invention relates to tear-resistant, composite sheet materials which are highly absorbent towards aqueous fluids, including blood and exudate, and are useful as drying materials, wound dressings, and chromatographic materials.

BACKGROUND ART

The prior art teaches preparation of polytetrafluoroethylene composite sheets having low-level water-absorbency. U.S. Pat. No. 4,153,661 relates to sheets comprising particulate materials distributed in a matrix of interentangled polytetrafluoroethylene fibrils. In these sheets water is absorbed primarily by filling voids between particles, not by swelling of particles. These prior art sheets contain primarily inorganic particulates, although a few organic particulates which have low-level water-absorbency are mentioned. Such organic particulates include the proteins casein and zein, and certain polyurethanes. The patentee discloses the use of 5 to 10 weight percent of water-swellable thermoplastic materials for enhancing the tensile strength of the composites. No composites are described in which all or a major portion of the particulate is highly water absorbent or water-swellable. The composites of the above patent are not known to be useful as wound dressings.

It has been recognized in the prior art that a satisfactory wound dressing creates a suitable microclimate for rapid and effective healing. A good wound dressing prevents dehydration and scab formation, is permeable to oxygen, is sterilizable, absorbs blood and exudate, protects against secondary infection, supplies mechanical protection to the wound, is non-adherent, is non-toxic, is non-allergenic and non-sensitizing, does not shed loose material into the wound, conforms to anatomical contours, resists tearing, resists soiling, is not inflammable, has constant properties in a range of temperatures and humidities encountered in use, has long shelf life, has small bulk, is compatible with medicaments, and is economical.

Layered dressings are known in the art. U.S. Pat. No. 4,203,435 discloses a five-layered wound dressing having two permeable, non-adherent outer layers, the next two layers being cellulosic fiber absorbent layers, and the inner-most layer comprising a powder of modified starch. U.S. Pat. No. 3,888,257 provides a layered disposable, absorbent article for management of body fluid flow, in which a central zone of a matrix of fiberized wood pulp incorporates a three-dimensional dispersion of hydrocolloid polymer particles.

Great Britain Pat. No. 1,454,055 discloses a preparation, such as a bandage, for treating a fluid-discharging skin surface, which comprises a water-insoluble hydrophilic macromolecular swellable material such as crosslinked dextran, carboxymethyldextran, starch or hydroxyethyl starch for absorbance of low molecular weight constituents of blood plasma in admixture with a dermatologically suitable carrier. The swellable material may be dextran, or a derivative thereof, and the carrier may comprise fibrous material. This patent discloses no fibrous materials having submicron diameters.

A crosslinked dextran derivative which is sold by Pharmacia of Sweden under the tradename "Debrisan", is primarily used as a wound treating powder. Pharmacia's trade literature on Debrisan ® asserts the following advantages for the use of the powder: "continuously absorbs wound exudate and bacteria, cleanses the wounds, prevents crust formation, reduces inflammation and oedema and does not cause sensitization". The trade literature which states that no side effects have been reported also gives the following limitations on the product: "(1) do not leave Debrisan ® for more than 24 hours on wounds with a very low exudation rate as it may dry and form a crust which may be difficult to wash off, (2) occlusive dressings may lead to maceration of skin around the wound under treatment, (3) when deep infected wounds are treated, care must be taken to wash Debrisan ® from the depths of the wound, and (4) no side effects have been reported. Warning: Debrisan ® spillage can render surfaces very slippery. Clear spillages promptly." Thus, it appears that although the dextran derivatives have excellent absorptive capacities, there are problems associated with their use relating to moisture loss, adhesion, contamination of the wound, and handling hazards.

DISCLOSURE OF INVENTION

The process of the present invention provides water-swellable fibrillated polytetrafluoroethylene composite sheets which are tear-resistant and durable. The sheets are useful in chromatography, as drying materials, and for wound dressings, uses where high water absorbancy or water-swellability are important. Although non-sintering processes of the prior art can be used to make composite sheets which absorb some water, e.g., up to a weight of water equal to the weight of the composite sheet, when the processes of the prior art are used with the water-swellable materials of the present invention, tear-resistant, durable, composite sheets cannot be readily prepared. It has been found, surprisingly, that small changes in the procedures of U.S. Pat. No. 4,153,661 are critical to provide tear-resistant, water-swellable, composite sheets. As the water-swellability of the particulate portion of the composite increases, the tear-resistance of the sheets prepared by the processes of the prior art rapidly decreases. Using water-swellable particulates which absorb greater than twice their own weight in water, it is not possible to make tear-resistant composite sheets without modifying the process of the prior art.

In the present invention, polytetrafluoroethylene spheroids present in a doughy starting mixture of polytetrafluoroethylene emulsion and water-swellable particulate are converted into a network of interlaced microfibrous polytetrafluoroethylene. This network imparts tear-resistance and cohesiveness to the mass. To achieve this conversion great pressure is applied to the mixture by steel rollers of a rubber mill so that a critical amount of mechanical friction exists between the particulates and the polytetrafluoroethylene spheroids. The prior art (U.S. Pat. No. 4,153,661) required the addition of sufficient luricant water to exceed the absorptive capacity of the solids and yet maintain a putty-like consistency. However, with water-swellable particulates and especially with highly water-swellable particulates it has been found that such an addition is not successful.

Using highly water-swellable particulates, the addition of sufficient lubricant water to exceed the absorptive capacity of the solids results in swollen, bloated particles. A putty-like consistency was not obtained. The swollen particles had a soft lubricious consistency which precluded fibrillation of the polytetrafluoroethylene spheroids. It is now known that the addition of up to one equivalent weight of water to water-swellable particulates results in rapid absorption of the water into the particulates and provides poor lubrication and mixing. Uneven distribution of the polytetrafluoroethylene spheroids, resulting from poor lubrication and mixing, causes the resulting composite to be weak and non-coherent, similar to a "curdy" cheese, i.e., having a tensile strength of less than 0.1 megapascal.

The present invention overcomes some of these problems by providing a composite which is a sheet material comprising:

(a) a polytetrafluoroethylene (PTFE) fibril matrix;
(b) 1.0 to 10 parts, preferably 2.0 to 10 parts, of hydrophilic absorptive particles per part of PTFE by weight enmeshed in said matrix, the absorptive particles having absorptive capacity greater than 1.0 grams of water per gram of dry particles.

The composite sheet materials of the present invention are useful of themselves as wound dressings, and are particularly useful as components of wound dressings wherein a partially occlusive film is coated on one surface of the matrix of composite sheet material.

In this application:

"occlusive film" means a layer of material having controlled permeability or porosity to water; and "non-swellable particulates" refers to particulate-swelling in a PTFE matrix of the invention (20 weight percent PTFE and 80 weight percent particulate) and means particulates having a change in volume $((V_g-V_o)/V_o)$ of less than 0.5, where $V_g$ is the volume of particulates when water swollen and $V_o$ is the volume of dry particulates;

"tear-resistant" means having a tensile strength of at least 0.5 megapascals; and "cohesive consistency" means that the mass sticks together during handling, as for example, like pie crust dough.

When the partially occlusive film is present, such a coating has controlled permeability and it reduces the rate of evaporation of moisture out of the dressing to the atmosphere thereby reducing the tendency for formation of a hardened scab over the wound. Scab formation is undesirable because it retards healing and enhances scar formation. In addition, by slowing the moisture loss from the wound surface, the moisture barrier imparts to the wound dressing of the instant invention superior non-adherent properties.

The absorptive particles of the present invention are thoroughly enmeshed in the PTFE fibrils so that substantially all of the particles are contained in the fibrils and do not slough in the wet or dry state. Contamination of the wound from particulate matter originating in the dressing is thereby prevented.

The composite sheet wound dressing of the present invention has many desirable characteristics. For example, it provides an ideal microclimate for healing in that it is highly permeable, thereby allowing oxygen to permeate the membrane. The bandage is sterilizable. The composite is a good absorbent for blood and exudate (see Example 2) and does not adhere to the wound surface. These properties exist because the absorptive particles are not in direct contact with the wound but are separated therefrom by an intertwining coat of polytetrafluoroethylene fibrils. The dressing is particularly advantageous in that it need not be changed every day. The wound dressing affords rapid absorption of exudate and thereby draws bacteria away from the wound, helping to protect against wound sepsis, as will be discussed below. Dressings of the present invention can provide water absorptive capabilities as high as about 90 grams of water per gram of dressing. When a partially occlusive film is present as the outermost layer on the PTFE fibril matrix, the moisture transmission is controlled so that the wound stays moist enough to prevent scab formation and adherence of the dressing to the wound surface and to permit rapid epidermal wound healing.

The composite sheet wound dressing of the present invention consisting of a PTFE fibril matrix in which absorptive particles are enmeshed, but which has no moisture controlling coating, also has many of these desirable characteristics. Such dressings are most useful in treating wounds which produce large amounts of exudate, for example infected wounds. In such a situation, it is desirable to change the dressing frequently, since the absorptive capacity of the dressing tends to be quickly exhausted. However, rapid evaporation of moisture prolongs the length of time the dressing remains absorbent on the wound. Thus, dressings both with and without moisture evaporation retarding coatings are useful, depending on the rate at which a wound is producing exudate. It is most desirable to use a dressing which absorbs exudate at approximately the rate the wound is producing exudate to prevent either dehydration of the wound or excessive accumulation of exudate on the wound surface.

The composite sheet, a chamois-like material, is very conformable yet tough enough to provide some protection against the abrasive and penetrating effects of foreign objects. It maintains its physical integrity under normal handling conditions, is not soiled due to its chemical inertness and low surface tension, does not physically or chemically degrade (i.e., it has good shelf life) and the chemical and physical properties are not adversely affected by changes in temperature from −20° C. to 120° C. Polytetrafluoroethylene is presented at the surface. The absorptive particles are not on the surface of the composite but are strongly enmeshed in tough PTFE fibrils. Therefore, there is little chance that any absorptive particles will slough off. The PTFE fibrillated surface is not rendered adhesive by other materials because it is non-absorptive and non-wetted due to its unusually low surface tension despite the fact that the composite is very hydrophillic. In addition, PTFE is non-toxic, non-allergenic and nonsensitizing. The physical property of water absorbency of the composite sheets of the present invention are considerably superior to those of prior art aqueous-absorptive sheets.

BRIEF DESCRIPTION OF DRAWING

The drawing shows a cross-sectional view, greatly enlarged, of a composite sheet of the present invention.

DETAILED DESCRIPTION

The present invention provides a composite which is a sheet material, comprising:
(a) a polytetrafluoroethylene fibril matrix; and
(b) 1.0 to 10 parts, preferably 2.0 to 10 parts, of hydrophilic absorptive particles per part of PTFE by weight enmeshed in said matrix, said absorptive particles having absorptive capacity greater than 1.0 gram of water per gram of dry particle;
wherein substantially all of the hydrophilic absorptive particles are unavailable for sloughing.

FIG. 1 shows one embodiment of a composite sheet 10 according to the present invention having matrix 14 of PTFE fibrils 16 in which are enmeshed hydrophilic absorptive particles 18.

To prepare the composite sheet the hydrophilic particles are incorporated into a PTFE emulsion to form a paste, which is subjected to a great amount of shear causing the PTFE to fibrillate and enmesh the particles into a fibrillar matrix. There are many processes of fibrillating PTFE and virtually all non-sintering processes are adaptable to the method of making the composite of the instant invention. The most suitable, however, is that described by Ree et al. in U.S. Pat. No. 4,153,661, and is hereby incorporated by reference. Basically, the fibrillation involves the formation of a paste of water swollen particulate material and PTFE particles, intensive mixing at 50° to 100° C., biaxial calendering, and a drying step. This results in a membrane with PTFE fibrils having a thickness in the range of about 0.025 to 0.5 micrometers.

It has now been found that in order to obtain a paste which will provide durable, tear-resistant, composite sheets with water-swellable particulates enmeshed therein, according to the present invention, the process includes the steps of (1) dry blending one or more hydrophilic, absorptive particulate materials;

(2) admixing water to particulate in a weight ratio in the range of 1:2 to 10:1, preferably 1:1 to form a damp mixture;

(3) adding graually, with stirring, to said mixture an equal weight of an aqueous emulsion of polytetrafluoroethylene having in the range of 15 to 25 weight percent solids (preferably about 20 weight percent solids) so that the resulting mass has a cohesive consistency;

(4) mixing said mass in an intensive mixer at a temperature between 50° C. and 100° C. for a time sufficient to cause initial fibrillation of said polytetrafluoroethylene particles;

(5) optionally adding 0.2 to 1.0 part water to lubricate said mass;

(6) biaxially calendering said mass between calendering rolls maintained at about 50° C. to about 100° C. to cause additional fibrillation of said polytetrafluoroethylene particles to form a self-supporting sheet while maintaining the water content of said mass at least at a level above the absorptive capacity of the solids and also closing the gap between the calendering rolls with each successive calendering operation, for a time sufficient to produce a high tensile strength sheet having a tensile strength of at least one megapascal; and (7) drying the resultant sheet to remove water.

The ratio of water to particulate in step (2) varies with the particulate used and increases with the swellability of the particulate. Each type of particulate has a unique preferred ratio, as noted in TABLE I, below. It is preferred to add some water as a lubricant, generally from about 0.2 to 1.0 part after shearing is completed, and before mill calendaring.

If not enough water is added in step (2), the polytetrafluoroethylene emulsion will not mix well with the particulate. If too much water is added in step (2) the mixture with polytetrafluoroethylene will provide a soft, relatively weak composite which may not be capable of forming a sheet when milled and calendared. Gradual addition of the polytetrafluoroethylene emulsion in step (3) is preferred; this prevents poor mixing which may result in the composite obtained eventually being weak and non-homogenous rather than tear-resistant.

The water-swellable particulates useful to make composite sheets of the present invention are readily distinguished by microscopic examination from particulates which are non-water absorbent and non-water-swellable. Under microscopic examination it is observed that good absorbents which are water-swellable show little or no liquid phase between particles when an equal weight of water is added, whereas non-water-swellable particulates show the liquid absorbed as a phase distributed among the particles when an equal weight of water is added to a batch of particulate.

The size of the absorbent-type particles are within a broad range of 0.1 to 300 micrometers when dry. Preferably, the particle size range of the water-swellable particulate absorbent is 1.0 to 80 micrometers. The particles which are insoluble in an aqueous environment have an absorptive capacity greater than 1.0 (i.e., in the range of 1.0 to 100 grams), preferably 2.0 to 10.0 grams of water per gram of dry particles.

Because of its high absorptive capacity, the sheet may be used to cleanse the surfaces of contaminated or infected wounds. Such wounds include traumatic wounds, cuts, lacerations and abrasions, burns, indolent wounds, pressure sores, and ulcers which may be contaminated with foreign matter, dead tissue, and microorganisms such as bacteria and fungi. For this cleansing purpose dressings of the instant invention may be removed and replaced as often as necessary to remove contaminating material, and then a final similar dressing may be left in place undisturbed on the cleansed surface until the wound heals. Alternatively, if the wound is too deep to heal spontaneously, after cleansing the wound surface in the above manner, it may be grafted. It is to be noted that some of the cleansing action is brought about by the activities of cells, (e.g., leukocytes and macrophages) in the tissues of the body, aided by appropriate conditions of hydration and oxygen availability brought about by the dressing. The breakdown products are removed by the absorbent in the dressing, thus completing the cleansing process.

The hydrophilic absorbent may be water-swellable particles such as alginic acid, polyacrylate-cellulose graft copolymer, collagen, chitin, chitosan, dextran, carboxymethyldextran, starch, modified starch, hydroxyethyl starch, hydrolyzed polyacrylonitrile, starch-methacrylonitrile polymer, polyacrylamide, hydrolyzed polyacrylamide (Separan ® AP-30, Dow Chemical Co.), carboxymethylcellulose, and derivatives or mixtures of the aforementioned materials. The preferred materials are crosslinked dextran derivatives having a water absorptive capacity between 2 g and 10 g of water per gram of dry material, phosphate-crosslinked carboxymethylated starch, phosphate-crosslinked hydroxypropyl substituted starch, designated MS-2 in TABLES III and IV below (the hydroxypropyl group being randomly attached to the 2-, 3-, or 6-carbon of the glucose monomer by an ether linkage), carboxylate-ester crosslinked carboxymethylated polyglucose, and similar materials. These are preferred for wound dressing uses.

The thickness of sheets providing satisfactory volume absorption when used as composite sheet materials is in the range of 0.1 to 10 mm, preferably in the range of 0.25 mm to 5 mm.

Hydrophilic absorbent particles may be admixed with inert less-absorptive diluent particulates which range in size from 0.1 to 100 micrometers to improve the feel and handling characteristics of the composites and to facilitate their manufacture. It has been found that very highly water-swellable composite sheets (e.g., having absorptive capacity by volume of 10 times or more when compared to dry particulates) are stiffer and less flexible than those which swell less, when these sheets are dried. However, the addition of up to 70 weight percent non or slightly water-swellable particulates, compared to total particulate, to such composites imparts greater flexibility and softness to such composites while retaining good strength. Examples of diluent particles include powdered polymers such as polyethylene, polypropylene, polystyrene, kaolin, talc, silica, bentonite, and vermiculite.

The particulate material accounts for from 40 to 90%, and preferably 80–90%, by weight of the total composition, of which up to 70% can be inert diluent particles. The most preferred amount of total particulates is about 85% by weight.

As noted above, if the uncoated PTFE-absorptive particulates composite membrane is used as a wound-treating material for extended periods of time, there is a tendency for formation of a hardened scab over the wound due to excessive moisture transmission out of the dressing to the atmosphere. Thus, to render the dressing satisfactory for long periods, evaporation rates must be reduced by means of a coating on one side of the bandage. No coating is required for short (1–4 hours) application times, especially for wounds which produce large amounts of exudate.

Medicaments which may be useful in promoting wound healing or reducing infection of wounds can be incorporated in the composite wound dressings. These can include but are not limited to antibacterial agents, such as the penicillins, the aminoglycosides, iodine and other well known antibiotics useful in reducing infection; antifungal agents such as nystatin and undecylenic acid; hemostatic agents such as microcrystalline cellulose, chitosan, thrombin, and fibrin; and, wound-healing promoting agents such as epidermal growth factor, ascorbic acid, collagen, and aluminum salts such as aluminum acetate and aluminum chlorohydrate.

Small amounts (e.g., 5.5 to 6.5 weight percent based on weight of PTFE) of non-ionic surfactants such as octylphenol polyoxyethylene or nonylphenol polyoxyethylene may be incorporated in the composite sheets to aid the wetting process.

A moderate amount of water-swellability, for example up to ten times the volume of the absorbent particulate, is preferred for wound dressing applications using the composite sheets of the invention. It has now been found that durable, tear-resistant, water-swellable composite sheets have a variety of additional uses. In some of the additional uses preferred particulates will vary in order to maximize selected properties. Tear-resistant, water-swellable composite sheets are surprisingly useful for drying non-aqueous solvents. For example, gasoline saturated with water at room temperature in the tank of an automobile or airplane frequently precipitates ice when exposed to below freezing temperatures. Simple filtration through the composite sheets of the invention that contain up to 90 percent by weight highly-water swellable particulates removes enough water to preclude such precipitation. It has been found that it is possible to remove substantially all traces of water from organic fluids such as hydrocarbons, chlorinated solvents, toluene, diethyl ether, tetrahydrofuran and a variety of other non-water miscible solvents by passing the solvents over or through composite sheets of the invention. Preferred particulates for this application are cross-linked dextrans, starch modified by branch polymerization with acrylic acid, cross-linked sulfonated polystyrenes, cross-linked acrylate ester-acrylic acid copolymers, and the polyacrylamide sold as Biogel ®. Preferred sheets used for such drying applications surprisingly retain their physical integrity for extended use, and greatly reduce the use of human time, and therefore cost of drying.

The water-swellable composite sheets of the present invention are also useful as chromatography supports, for example, by selecting a particulate such as Biorad ® cation exchange resins which selectively absorb through ionic forces or polarity. They are useful for gas phase or liquid phase chromatography because of their porous nature and very uniform distribution of the substrate which prevents "channeling".

Objects and advantages of this invention are further illustrated by the following examples, but the particular materials and amounts thereof recited in these examples, as well as other conditions and details, should not be construed to unduly limit this invention.

EXAMPLE 1

Preparation and Characterization of Composite Dressing Materials

Fifty grams of Sephadex ® G-25-80 (crosslinked dextran derivative, particle size 20–80 microns, available from Sigma Chemical Co., St. Louis, MO) and 50 gm of water were mixed in a one-liter beaker. The Sephadex ® absorbed all the water and swelled from 60 cc to a total volume of 210 cc. Sixty grams of water and 20 grams of polytetrafluoroethylene (PTFE) resin dispersion (Teflon ® 30B, Dupont) were mixed and added to the swollen Sephadex ® in 10 ml portions with intermittent vigorous stirring. After these ingredients had been thoroughly mixed, a semi-coherent material was formed with enough physical integrity to allow the entire contents to be removed from the beaker as a single mass.

The above mass was passed through two rollers kept at 50° C. and spaced about 0.4 cm apart to give a strip of cohesive material which barely supported its own weight of dimensions approximately 14 cm×0.4 cm×42 cm. The resulting strip was folded to three thicknesses or a material having dimensions of 14 cm×1.2 cm×14 cm and then passed through the rollers after a 90° rotation from the previous pass. The cyclic process of three-layer folding and re-rolling in the direction 90° from the direction of the preceding pass was repeated a total of 14 times to give a tough, strong, flat piece of material of dimensions 14 cm×0.4 cm×42 cm. The material was then calendered along the long axis through a set of ten rollers which were spaced at successively smaller distances apart to give a continuous ribbon of dimensions 14 cm×0.04 cm×480 cm. The ribbon was folded to give a 32-layered piece of dimensions 14 cm×1.3 cm×15 cm. The 32-layered piece was then calendered as before along the 14 cm axis (90° from the calendering direction used previously) to give a ribbon of dimensions 15 cm×0.05 cm×350 cm. By calendering using varying spaced rollers, different degrees of compaction of the mass could be obtained and various thicknesses of ribbon, as desired, realized. The calendered sheet of material was washed in a water bath and then allowed to dry in air for 48 hours. It was then stretched to a width of 20 cm to give it a softer, more comfortable feel. The resulting water-swellable composite sheet may be used uncoated or it may then be coated with a semi-occlusive polymeric film.

The tensile strength of the composite sheets was measured according to ASTM 638. The measurements were made on strips of material cut parallel to the longitudinal axis of the final calendering step. The tensile strength was about 300 psi (2 megapascals). A tensile strength in the range of 75 to 1000 psi (0.5 to 6.67 megapascals) can be obtained by variation of the preparation procedures.

The water vapor permeability of the uncoated composite sheet was measured according to ASTM E 96-66, Procedure B, at 23° C. with an 81 percent relative humidity gradient across the dressing. A 5.7 cm² area was evaluated. The data showed that the permeability of the test material was $2 \times 10^3$ grams $H_2O/m^2/24$ hours.

The rate of evaporative water loss was determined according to ASTM E 96-66, Procedure BW, at 23° C. with a 100% relative humidity gradient across the test material. The rate of evaporative water loss was found to be $2.5 \times 10^4$ gm $H_2O/m^2/24$ hrs.

To determine the water absorption, small pieces of material (0.1 to 0.5 g) were weighed and placed in water for 2 hours. They were removed, blotted with a paper towel to remove non-absorbed water, and reweighed. The dressing materials absorbed 2.5 g $H_2O$ per gram of dry material.

EXAMPLE 2

Evaluation of PTFE Composite Dressing Material on shallow wounds of pigs

The PTFE composite material was made by the process of Example 1.

Control—Polyethylene film (natural grade, low density) 37.5 micrometers thick.

The dressings were double packed and sterilized by ethylene oxide gas followed by degassing (24 hours in an aerator).

The hair on the back of the pigs was clipped with electric clippers 48 hours prior to the start of the surgical procedure. Protective guards were put on the animals at this time. At the start of the procedure, the anesthetized pigs were shaved, taking care not to damage the skin. Sterile techniques were used throughout the procedure and all operatives wore masks, hats, sterilized gowns and gloves. Care was taken to rinse any glove powder from the gloves.

Standard shallow wounds, each measuring 2.5 cm×2.5 cm, were made on each animal using sharp round-bellied scalpel blades. The scalpel was held in the plane of the skin and the epidermis and papillary layer of the dermis were cut away. When all wounds had been made, the dressings were applied. Four wounds were covered with the dressing of the invention, and four with the control.

Biopsy specimens were obtained after one, three, and six days from each of the wounds. Using a template measuring approximately 1 cm×4 cm, cuts were made through the dressing to the wound surface and extended the full thickness of the skin. The specimens were placed in 10% buffered formal saline.

After 24 hours fixation the biopsy specimens were trimmed to yield four blocks. For each wound, two of the blocks spanning the entire width of the wound were embedded in wax and serial sections prepared using a rotary microtome set to cut at 10 microns. Every fifth section was mounted on glass slides to provide a series of sections for staining with H & E, Weigert and van Geison's stain and Masson's trichrome method.

Sections were examined under the microscope and the wound surfaces of the control and PTFE composite dressing were compared.

RESULTS

Day 1

Polyethylene Film Control Dressing: All four wounds that had been covered with the polyethylene film control dressing were similar. There was a fibrinous exudate on the cut surface of the dermis which was approximately 0.1 mm thick. The exudate appeared to be hydrated because there were no signs of damage by dehydration. The exudate contained moderate numbers of erythrocytes and cells characteristic of the acute inflammatory response; polymorphonuclear leucocytes, monocytes and eosinophils. Near the surface, just below the dressing, many of the polymorphs were "stringy" and pycnotic indicating that they were dying. In the dermis the small superficially placed blood vessels were dilated and the perivascular connective tissue stroma was filled with cells similar to those seen in the exudate. The collagen bundles were moderately swollen, indicating some edema. There was some swelling of the epidermis at the margins of the wound, but no epidermal regeneration had yet taken place.

Dressing of the Invention: The four wounds treated with the PTFE/Sephadex ® composite sheet were similar to one another. The dressing could be seen on the wound surface in the histological sections. It measured approximately 0.76 mm thick. Exudate penetrated only one-third of the way into the dressing. The Sephadex ® beads were about 80 microns in diameter and were enmeshed in a network of fine PTFE fibrils. Those beads towards the surface stained deeply blue with the basic haematoxylin stain. Beads in the region impregnated with exudate stained a much paler shade of blue. This may have indicated a difference in pH, the beads surrounded by exudate being more acid. The exudate filled the interstices of the membrane around all of the beads, confirming that the dressing had an open, porous structure. There were no cells in the exudate within the dressings and the exudate was homogenous under moderate magnification in the optical microscope and did not contain the fibrin network seen under the polyethylene dressing. For the most part, the dressing was directly on the cut surface of the dermis without an intervening layer of blood clot or exudate. There was no epidermal regeneration.

Day 3

Control Dressing: At the end of the third day there was a thick (approximately 0.5 mm) cellular exudate between the polyethylene dressings and the wounds. This contained numerous inflammatory cells, mostly polymorphonuclear leucocytes. The exudate was heavily infected with colonies of bacteria (cocci), especially at the wound margins and in places where the epidermis was most mature. Most of the cells in the exudate were dead or dying.

The wounds were almost entirely covered by newly regenerated epidermis. For the most part, it was lying on a layer of fibrinous exudate but in some places it was in direct contact with the dermis. The new epidermis was several cells thick and was differentiated into a basal cell layer, a middle layer of rounded cells and an upper layer of flattened cells with pycnotic nuclei. There was no differentiated horny layer. The epidermal-dermal border was undulating.

In the dermis there were still numerous polymorphonuclear leucocytes but the predominant cell was the mononuclear fibroblast. Blood vessel and connective tissue regeneration was just beginning beneath the new epidermis.

Dressing of the Invention: At the end of the third day the dressing did not contain any more exudate than on the first day; the exudate had penetrated only the lower third of the membrane. Between Day 1 and Day 3 the surface of the wound beneath the dressing dehydrated and formed a scab. This scab was about 0.25 mm deep and consisted of dried collagenous tissue impregnated with leucocytes. Epidermal regeneration was taking place, but only about 50% of the wound surface was covered by new epidermis migrating from cut hair follicles and from the margins of the wound beneath the scab. The new epidermis had a flat epidermal-dermal border and was only two or three cells thick.

There were few inflammatory cells in the underlying dermis. There were no signs of bacterial colony formation. Connective tissue repair had not yet begun.

Day 6

Control Dressing: Under polyethylene, the new epidermis was now well differentiated and was keratinizing. There was a layer of infected exudate and in some places micro-abcesses had formed, breaching the surface of the new epidermis. Exaggerated epidermal ridges were formed and connective tissue regeneration was taking place under the new epidermis.

Dressing of the Invention: Under this dressing epidermal cell migration had now covered the wound but the new epidermis was less mature than on the control wound. There were, however, no signs of infection.

The events within the dressings, as seen histologically, were interpreted to mean that the dressings of the invention initially absorbed the fluid blood and exudate present on the wound surface when the dressings were applied. It is known that because of the inflammatory reaction and increased vascular permeability, the wounds continue to ooze proteinaceous exudate for at least 24 hours after injury. Evidently, the exudate filling the lower third of the dressing soon dried, blocking the pores and preventing further uptake. Further loss of water vapor dehydrated the surface of the wound, damaging the exposed tissue and causing a scab to develop. In consequence, epidermal wound healing was delayed, but did proceed successfully.

The opposite effect was seen under the occlusive polyethylene film control dressing. The exudate remained hydrated for at least three days, no scab formed, and the epidermis migrated through the moist exudate between the polyethylene film and the wound surface. Bacteria proliferated in the exudate and their presence stimulated an outpouring of leucocytes. The natural defense mechanisms were adequate to control the infection, but the presence of numerous bacterial colonies at three days in areas where the new epidermis prevented access of leucocytes to the infection, the occurrence of micro-abcesses at six days and the persistance of acute inflammation, indicated that this was a borderline septic situation. It is anticipated that the presence of more virulent organisms or a less adequate leucocytes response would result in septic wounds and delayed healing.

Whereas under the occlusive polyethylene film dressing a mesh of fibrin was clearly seen in the exudate, no fibrin network was visible in the exudate within the composite dressing.

It is concluded that the composite dressing that incorporated beads of dextran polymer in a matrix of polytetrafluoroethylene fibrils provided beneficial effects on donor site wounds.

EXAMPLE 3

Samples of water-swellable composite sheets were prepared from mixtures of PTFE (Teflon 30B) and various hydrophilic particulate materials, according to the procedures disclosed in Example 1. TABLE I contains the amounts of particulate material, water and PTFE used in each mixture. The thickness of the composite sheets varied from 0.1 mm to 2.0 mm. All composite sheets were useful in the practice of the present invention as drying materials.

TABLE I

| Particulate Material | Weight of Particulate | Volume of Water | Volume Teflon ® 30B[h] | Composition of Product (Dried) |
| --- | --- | --- | --- | --- |
| Chitosan[a] | 40.0 gm | 80. ml | 15. ml | 25% PTFE, 75% Chitosan |
| Alginic Acid[b] | 60.0 gm | 120. ml | 25. ml | 27.5% PTFE, 72.5% Alginic Acid |
| Collagen[c] | 8.0 gm | 8. ml | 4. ml | 31% PTFE, 69% Collagen |
| Kaolin[d] - Derivatized Starch[e] | 50.0 gm of each | 100. ml | 30. ml | 21% PTFE, 39.5% Kaolin 39.5% Derivatized Starch |
| Sepharose ®[f] | 20.0 gm | 140. ml | 10. ml | 31% PTFE, 69% Sepharose |
| Diethyl Amino Ethyl Sephadex[g] | 10.0 gm | 150. ml | 20. ml | 64.5% PTFE, 35.5% Diethyl Amino Ethyl Sephadex |

[a]Chitosan - Kytex M, Hercules
[b]Alginic Acid - Type III, Sigma Chem. Co.
[c]Collagen - purified from rat-tail tendon
[d]Kaolin-Kaopaque ®, Fisher Scientific Co.
[e]Derivatized Starch - SGP 5125, General Mills Chemicals
[f]Sepharose ® - Type 4B-200, Sigma Chem. Co.
[g]Diethyl aminoethyl Sephadex ® - A-50-120, Sigma Chem. Co.
[h]Polytetrafluoroethylene - Teflon ® 30B, Dupont

EXAMPLE 4

Samples of composite dressing materials containing various medicaments which may promote wound healing, reduce wound infection or be hemostatic were prepared according to the procedures disclosed in Example 1. The compositions of these dressings are presented in TABLE II. The medicaments were introduced into the dressings by three methods. Method A—Medicaments were added to the PTFE-particulate mixture before fibrillation of the PTFE on the two roll mill, thus ensuring the medicaments were thoroughly enmeshed in the fibrillated PTFE matrix. Method B—The fully manufactured dressing sample was soaked in an aqueous solution of medicament, allowing the sample to absorb medicament and then was dried, trapping the medicament in the sample. Method C—A solution of medicament was coated onto the surface of the sample and then allowed to dry.

TABLE II

| Dressing Composition | Medicaments | Preparation Procedure |
|---|---|---|
| PTFE 24.3% Sephadex ® G-25-80 72.9% | Ascorbic Acid 2.0% Boric Acid 0.4% Aluminum Acetate 0.4% | Method A |
| PTFE 20.0% Sephadex ® G-25-80 79.8% | Neomycin Sulfate 0.2% (antibacterial) | Method B |
| PTFE 20% Sephadex ® G-25-80 80% | Nystatin (antifungal) | Method C - An aqueous solution containing 100,000 units was coated onto the dressing surface and allowed to dry. |
| PTFE 21% Kaolin 39.5% Derivatized Starch SGP 125 39.5% | Iodine (antibacterial) | Method B - Soaked in 0.5% KI₃ aqueous solution. Material turned characteristic gun-metal blue. |
| PTFE 25% Chitosan 75% | Chitosan (hemostatic agent) | Method A |
| PTFE 20% Sephadex ® | Povidone Iodine | Method B - The dressing was |

TABLE II-continued

| Dressing Composition | Medicaments | Preparation Procedure |
|---|---|---|
| G-25-80 80% | | soaked in a 10% Povidone-Iodine solution and dried. |

The dressings were useful in treatment of wounds.

EXAMPLE 5

Measuring Volume of Water Absorbed per Unit Volume of Composite Membrane

A composite sheet consisting of about 80 weight percent hydrophilic particulate and about 20 weight percent PTFE microfibers was prepared as described in Example 1. This procedure gave a hydrophilic product of relatively uniform thickness (t) having about 50 percent voids when air dried. These voids are refilled readily when the film is immersed in water. A suitable representative sample of area A was cut from this film of thickness (t). The test sample of volume A·t=about 3 ml was weighed to the nearest hundredth of a gram. The weighed sample was immersed in water for 30 minutes. The wet film sample was sandwiched between two absorbent paper towels to remove excess water from the top and bottom surfaces. The water saturated composite film was reweighed to the nearest hundredth of a gram. The gain in weight (W) divided by the volume (V) of the sample gave the volume of water absorbed per unit volume of film (i.e., the swellability). The data obtained for films having various particulate components are listed below in Table III. The data obtained for films having hydrophilic modified starch powder (MS) or related particulate components are also listed below in Table IV.

TABLE III

Absorption of Water by Particulates in PTFE Microfiber Composite Sheets

| Sample Sheet | Percentage composition of the particulates major component | minor component | Percent PTFE | ml sol'n absorbed per ml of film |
|---|---|---|---|---|
| 1 | Vermiculite (85%) | | 15 | 0.51 |
| 2 | Kaolin (85%) | | 15 | 0.57 |
| 3 | Zeolite (85%) | | 15 | 0.53 |
| 4 | CaCO₃ (60%) | | 40 | 0.40 |
| 5 | Sephadex$^a$ G-25-80; 20-30 (85%) | | 15 | 2.22 |
| 6 | Sephadex$^a$ G-25-150; 50-150 (85%) | | 40 | 1.76 |
| 7 | Sepharose$^b$ 4B-2000 (75%) | | 25 | 1.30 |
| 8 | Chitin$^c$ (85%) | | 15 | 1.85 |
| 9 | Chitosan$^d$ (85%) | | 15 | 1.68 |
| 10 | Alginic acid$^e$ (85%) | | 15 | 2.86 |
| 11 | 1% Crosslinked sulf'd PS (70%) | | 30 | 25. |
| 12 | Super Slurper$^f$ (57%) | | 43 | 20. |
| 13 | Acid form of Super Slurper ® (85%) | | 15 | 1.67 |
| 14 | Film 13 resoaked in aqueous KOH | | | 7.67 |
| 15 | Film 14 resoaked in aqueous water | | | 93. |
| 16 | DEAE-Sephadex$^g$ (50%) | | 50 | 39. |
| 17 | Super Slurper (SS) (43%) | Kaolin (21%) | 36 | 6.3 |
| 18 | Super Slurper (33%) | Kaolin (33%) | 33 | 2.3 |
| 19 | DEAE-Sephadex (33%) | Kaolin (33%) | 33 | 4.0 |
| 20 | Biorad ® X8 (37%)$^h$ | Alginic acid (38%) | 23* | 2.8 |
| 21 | Sulf'd PS$^i$; Biorad X-1$^i$ (40%) | Surlyn ®$^k$ (40%) | 20* | 1.71 |
| 22 | above film resoaked in KOH | | | 1.69 |
| 23 | MS-2$^j$ (85%) | | 15 | 1.5 |
| 24 | Film 23 soaked in aqueous KOH | | | 4.7 |
| 25 | Film 24 soaked in water | | | 6.8 |

TABLE III-continued

Absorption of Water by Particulates in PTFE Microfiber Composite Sheets

| Sample Sheet | Percentage composition of the particulates | | Percent PTFE | ml sol'n absorbed per ml of film |
|---|---|---|---|---|
| | major component | minor component | | |
| 26 | Collagen (85%) | | 15 | 1.2 |

(a)Sephadex ® = Dextran (-1,4-linked polyglucose) crosslinked with epichlorohydrin.
(b)Sepharose = Agarose in the form of gelled beads
(c)Chitin = poly-N—acetylglucosamine
(d)Chitosan = poly-glucosamine
(e)Alginic acid = poly(-anhydro-d-mannuronic acid) i.e. $(C_6H_8O_6)_x$ from Algin
(f)Super Sluper ® (SS) = poly(acrylic acid) grafted onto corn starch
(g)DEAE-Sephadex = Diethylaminoethyl modified Sephadex
(h)Biorad X-8 = sulfonated polystyrene crosslinked with 8% divinylbenzene
(i)Biorad X-1 = sulfonated polystyrene crosslinked with 1% divinylbenzene
(j)MS-2 = phosphate crosslinked starch modified with hydroxypropyl groups (obtained from Collett-Marwell Hauge a/s, Asker, Norway). This material can be prepared as follows: the starch is reacted with propylene oxide according to the procedure of U.S. Pat. No. 2,733,238; the product is isolated and then cross-linked with sodium tri-meta-phosphate according to the prodecure of U.S. Pat. No. 2,801,242.
(k)Surlyn = copolymer of polyethylene and acrylic acid (E. I. DuPont de Nemours)
(l)PS = polystyrene The data in Table III show the result of two forms of absorption, (1) absorption by filling void spaces in a mass of particulate matter with water because the particulate matter is hydrophilic and (2) absorption by swelling the particulates into individual gell-like domains.

The dry composite sheets consist of particulates enmeshed in polytetrafluorethylene microfibers to provide 50 to 70 percent of the total volume as void space. A composite sheet made from non-water-swellable particulate exhibits water absorption of about 40 to 70 percent, i.e., 0.4 to 0.7 ml/ml of composite sheet (as in sample sheets 1 to 4 in TABLE III). Any uptake of water above this amount is attributable to swelling of the particulate to form isolated gell-like domains.

Composite sheets which exhibit absorption greater than 1.2 ml of water per ml of composite sheet are particularly useful as drying agents for organic solvents such as gasoline, toluene, diethyl ether and the like.

TABLE IV

Absorption of Aqueous Solutions by Composite Membranes Made from PTFE and MS (or Related Particulates)

| Sample No. | Composite membrane (% Particulates) | ml of aqueous solution absorbed/ml of film in the sequence 1 through 4 | | | |
|---|---|---|---|---|---|
| | | 1 Water | 2 5% KOH | 3 Water | 4 5% HCl |
| 1 | Sephadex (85%) | 2.2 | — | — | — |
| 2 | Sephadex (60%) | 1.8 | — | — | — |
| 3 | Sephadex (40%) | 0.8 | — | — | — |
| 4 | Acidified SS (85%) | 1.7 | 7.7 | 93.0 | — |
| 5 | MS-1$^a$ (85%), Primojel ® (Generichem Corp., Little Falls, NJ) | 1.5 | 4.7 | 6.8 | — |
| 6 | MS-2$^b$ (85%) | 2.1 | 2.1 | 1.7 | 2.1 |
| 7 | Carboxymethyl starch (85%) | 2.0 | 4.2 | 6.7 | 5.3 |

$^a$MS-1: phosphate-crosslinked starch modified with carboxymethyl groups.
$^b$MS-2: phosphate-crosslinked starch modified with hydroxypropyl groups.

Various modifications and alterations of this invention will become apparent to those skilled in the art without departing from the scope and spirit of this invention, and it should be understood that this invention is not to be unduly limited to the illustrative embodiments set forth herein.

What we claim is:

1. A method of preparing a tear-resistant composite sheet material having hydrophilic, absorptive particles enmeshed in a network of interlaced microfibrous polytetrafluoroethylene forming a fibril matrix, said hydrophilic absorptive particles being present in said matrix in the range of 1.0 to 10 parts particles per part polytetrafluoroethylene by weight, and said hydrophilic absorptive particles having absorptive capacity greater than 1.0 gram of water per gram of dry particle, said method comprising:
   (1) dry blending one or more hydrophilic, absorptive particulate materials;
   (2) admixing water to particulate in a weight ratio in the range of 1:2 to 10:1, to form a damp mixture, the water being present in a quantity insufficient to exceed the absorptive capacity of the particulate;
   (3) adding gradually, with stirring, to said mixture an equal weight of an aqueous emulsion of polytetrafluoroethylene having in the range of 15 to 25 weight percent solids so that the resulting mass has a cohesive consistency;
   (4) mixing said mass in an intensive mixer at a temperature between 50° C. and 100° C. for a time sufficient to cause initial fibrillation of said polytetrafluoroethylene particles;
   (5) biaxially calendering said mass between calendering rolls maintained at about 50° C. to about 100° C. to cause additional fibrillation of said polytetrafluoroethylene particles to form a self-supporting sheet, while closing the gap between the calendering rolls with each successive calendering operation, for a time sufficient to produce a tear-resistant sheet having a tensile strength of at least 0.5 megapascal; and
   (6) drying the resultant sheet to remove water.

2. The method according to claim 1 further comprising the step of adding 0.2 to 1.0 part water, after fibrillation step (4), to lubricate said mass.

3. The method according to claim 1 wherein said hydrophilic absorptive particles are present in a range of 2.0 to 10 parts per part PTFE by weight.

4. The method according to claim 1 wherein said hydrophilic absorbent particles are alginic acid, polyacrylatecellulose graft copolymer, collagen, phosphate crosslinked starch substituted with hydroxypropyl or carboxymethyl groups, chitin, chitosan, crosslinked dextran, crosslinked carboxymethyldextran, crosslinked diethylaminoethyl dextran, starch, hydroxyethyl starch, hydrolyzed polyacrylonitrile, starch-methacrylonitrile polymer, polyacrylamide, hydrolyzed polyacrylamide, cellulose, carboxymethylcellulose or derivatives or mixtures thereof.

5. The method according to claim 1 wherein said hydrophilic absorptive particles are particles of a cross-linked dextran derivative.

6. The method according to claim 1 wherein said hydrophilic absorptive particles are admixed with inert diluent particles.

7. The method according to claim 6 wherein said inert diluent particles are selected from polyethylene, polypropylene, polystyrene, kaolin, talc, silica, bentonite, and vermiculite.

8. The method according to claim 6 wherein said particles comprise 40 to 90 percent of the weight of the said composite sheet material.

9. The method according to claim 6 wherein said particles comprise about 80 to 90 percent of the weight of said composite sheet material.

10. The method according to claim 1 wherein said hydrophilic absorbent particles range in size from about 0.1 to 300 micrometers.

11. The method according to claim 1 wherein said hydrophilic absorbent particles range in size from about 1.0 to 80 micrometers.

12. The method according to claim 1 wherein said fibril matrix comprises fibrils having a thickness in the range of about 0.025 to 0.5 micrometers.

13. The method according to claim 1 wherein said composite sheet material has a tensile strength in the range of 0.5 to 6.67 megapascals (75 to 1000 psi).

14. The method according to claim 1 wherein said composite sheet material has a thickness in the range of 0.1 to 10 mm.

15. The method according to claim 1 wherein said composite sheet material further comprises medicaments selected from antibacterial agents, antifungal agents, hemostatic agents, and wound-healing agents.

16. The method according to claim 1 wherein said composite sheet material is a drying material.

17. The method according to claim 1 wherein said composite sheet material is a chromatographic sheet material.

* * * * *